United States Patent
Ebata et al.

(10) Patent No.: US 9,125,634 B2
(45) Date of Patent: Sep. 8, 2015

(54) DEVICE FOR CLOSING LUMINAL CAVITY AND METHOD THEREFOR

(71) Applicant: Terumo Kabushiki Kaisha, Tokyo (JP)

(72) Inventors: Katsunori Ebata, Kanagawa (JP); Tetsuya Fukuoka, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 201 days.

(21) Appl. No.: 13/742,882

(22) Filed: Jan. 16, 2013

(65) Prior Publication Data
US 2013/0197570 A1  Aug. 1, 2013

(30) Foreign Application Priority Data
Jan. 31, 2012  (JP) .................................. 2012-018884

(51) Int. Cl.
A61B 17/08  (2006.01)
A61B 17/00  (2006.01)
A61B 17/12  (2006.01)
A61B 17/064  (2006.01)

(52) U.S. Cl.
CPC ....... *A61B 17/0057* (2013.01); *A61B 17/12113* (2013.01); *A61B 17/12122* (2013.01); *A61B 17/12131* (2013.01); *A61B 17/12168* (2013.01); *A61B 17/12036* (2013.01); *A61B 2017/0641* (2013.01); *A61B 2017/12054* (2013.01); *A61B 2017/12095* (2013.01)

(58) Field of Classification Search
CPC ..................... A61B 17/0057; A61B 17/12036; A61B 17/12113; A61B 17/12122; A61B 17/12131; A61B 17/12168; A61B 2017/0641; A61B 2017/12054; A61B 2017/12095

USPC ......... 606/151, 191, 194, 200, 213; 623/1.11, 623/1.36

See application file for complete search history.

(56) References Cited

U.S. PATENT DOCUMENTS

| 5,843,164 A * | 12/1998 | Frantzen et al. ............. 623/1.16 |
| 7,128,736 B1 | 10/2006 | Abrams et al. |
| 2005/0049681 A1 | 3/2005 | Greenhalgh et al. |
| 2007/0088387 A1* | 4/2007 | Eskridge et al. ............. 606/213 |
| 2009/0299383 A1 | 12/2009 | Richter |
| 2011/0082491 A1* | 4/2011 | Sepetka et al. ................ 606/194 |

FOREIGN PATENT DOCUMENTS

| JP | 4060528 B2 | 3/2008 |
| WO | 99/05977 A1 | 2/1999 |
| WO | 01/21247 A1 | 3/2001 |
| WO | 01/30268 A1 | 5/2001 |

* cited by examiner

Primary Examiner — Ashley Fishback
(74) Attorney, Agent, or Firm — Kenealy Vaidya LLP

(57) ABSTRACT

A luminal cavity closing device can include a flexible shaft, a lid member, and a detachment mechanism. The flexible shaft extends in an axial direction. The lid member which is attached to a distal end of the shaft, can be rotated according to a torque transmitted from the shaft. Thus, a lock section can be thrust into a periphery of an opening of a luminal cavity formed in a living body lumen, to thereby lock the lid member to the periphery. The detachment mechanism can be configured to detachably attach the lid member to the shaft. The torque can be transmitted to the lid member, and the shaft can be detached from the lid member by the detachment mechanism while the lid member is locked to the periphery of the opening of the luminal cavity.

19 Claims, 8 Drawing Sheets

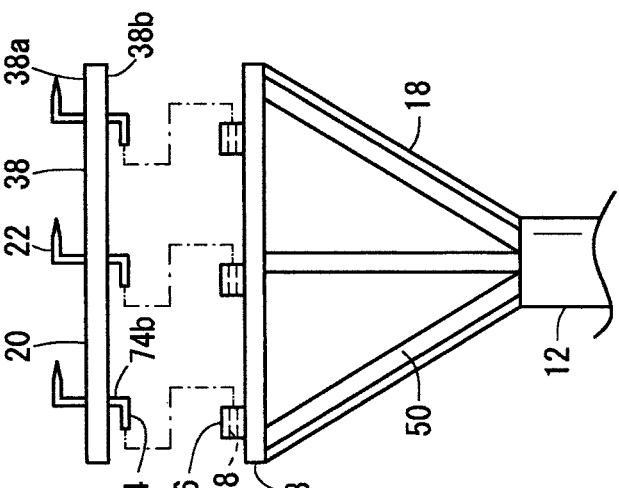
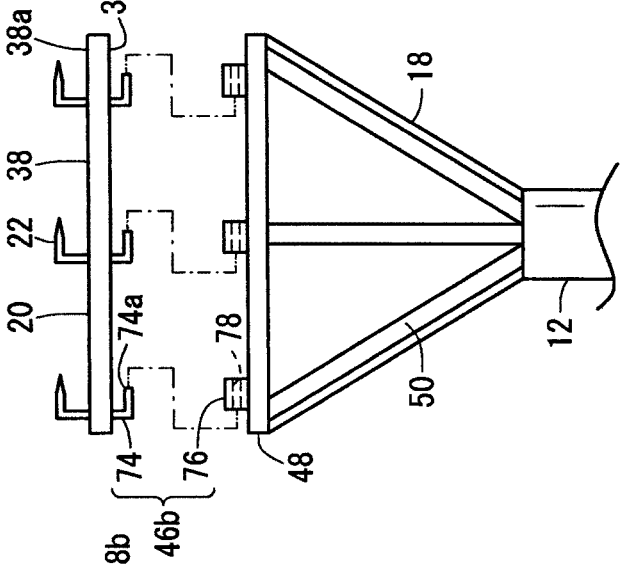
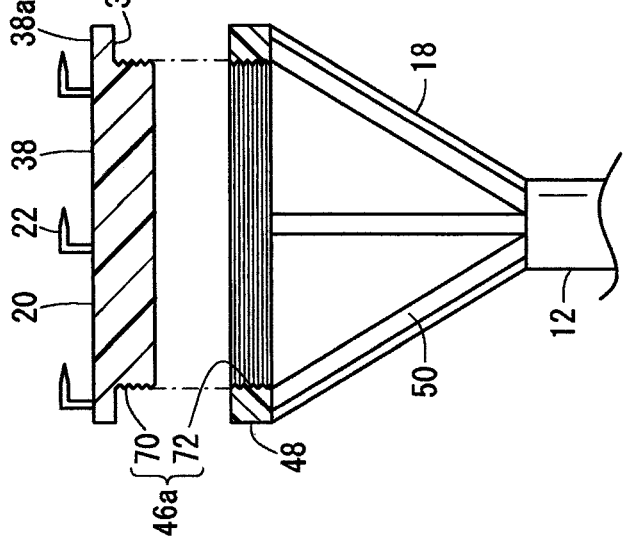

DEVICE FOR CLOSING LUMINAL CAVITY AND METHOD THEREFOR

This application claims the priority benefit under 35 U.S.C. §119 of Japanese Patent Application No. 2012-018884 filed on Jan. 31, 2012, which is hereby incorporated in its entirety by reference.

BACKGROUND

The presently disclosed subject matter relates to a luminal cavity closing device and a method/treatment for closing a luminal cavity (e.g., a hollow pouched structure having a lumen with an opening, including structures such as an aneurysm or varix or left atrial appendage or the like, hereinafter generically referred to as "luminal cavity") generated in a living organ or tissue.

A part of a blood vessel that is locally dilated and weakened is called an aneurysm or varix, and, particularly, one that is generated in an artery of the brain is called a cerebral aneurysm. Rupture of the cerebral aneurysm can cause subarachnoid hemorrhaging. There are several therapeutic methods for preventing such a rupture. One of the methods is the "neck clipping technique" in which craniotomy is conducted neurosurgically, and the portion between the cerebral aneurysm and the parent artery (a base portion of the aneurysm) is clipped. Another one is a method referred to as an "embolization technique," in which treatment is carried out without craniotomy. In this method, a catheter is inserted into the cerebral aneurysm via a blood vessel, and a flexible coil formed of a metal such as platinum is guided through the catheter and embedded in the cerebral aneurysm.

In accordance with one example of an embolization technique, as shown in Japanese Patent No. 4060528 (hereinafter referred to as Patent Document 1) and U.S. Pat. No. 7,128,736 (hereinafter referred to as Patent Document 2), an opening of a luminal cavity continuous with a blood vessel may be occluded, after an occlusive agent or a cage (corresponding to the above-mentioned coil) or the like is embedded in the luminal cavity (or without conducting such an embedding step). Incidentally, the expression "occlude" herein includes, unless otherwise specified, not only the meaning of a tight closure of the opening of the luminal cavity but also a concept of leaving part of the opening open without completely closing the opening, a concept of covering the opening with a meshed member, and the like concepts (in other words, the meaning of occlude includes operations related to blocking an opening so as to restrain the flow of blood through the opening into the luminal cavity).

For instance, in the case of the luminal cavity closing device disclosed in Patent Document 1, a device (lid member) having a shape memory structure capable of deployment (expansion) into a dish-like shape in a luminal cavity is delivered, and the lid member is disposed in the manner of bridging a neck (opening) of the luminal cavity, thereby occluding the luminal cavity. On the other hand, in the luminal cavity closing device disclosed in Patent Document 2, a mesh-formed lid member extending radially from a central portion is disposed at an opening of a luminal cavity, thereby occluding the luminal cavity. With the lid member disposed in this manner, the flow of blood into the luminal cavity is restrained.

SUMMARY

The embolization techniques using any of the luminal cavity closing devices disclosed in Patent Documents 1 and 2 can have attendant disadvantageous in that the lid member disposed at the opening of the luminal cavity may come out of position or be disengaged under the influence of the blood flowing through the blood vessel, pulsations of the blood vessel, bodily movements, or the like.

Thus, there is a need for a luminal cavity closing device and a luminal cavity closing method by which an opening of a luminal cavity formed in a living body organ can be occluded with great assurance, and in which a rise in the internal pressure of the luminal cavity can be effectively restrained, through a simple operation.

According to an embodiment of the presently disclosed subject matter, there is provided a luminal cavity closing device that can include: a flexible shaft extending in an axial direction; a lid member which is attached to a distal end of the shaft; and a detachment mechanism. The lid member can be rotated according to a torque transmitted from the shaft, and thrusts, attendantly on this rotation action, a lock section into a periphery of an opening of a luminal cavity formed in a living body lumen. Thus, the lid member can thereby be locked to the periphery of the opening of the luminal cavity. The detachment mechanism can be configured such that the lid member is detachably attached to the shaft, while torque can still be transmitted to the lid member, and thus enabling the shaft to be detached from the lid member with the lid member being locked to the periphery of the opening of the luminal cavity.

In the above-mentioned luminal cavity closing device, the lid member which is rotated according to torque transmitted from the shaft, and the detachment mechanism which detachably interconnects the shaft and the lid member are provided. Therefore, an opening of a luminal cavity can be occluded through a simple operation. Specifically, when the lid member is rotated by the shaft, the lock section is thrust into the periphery of the opening, and thereafter the lid member is detached from the shaft by the detachment mechanism. This ensures that the flow of blood into the luminal cavity can be restrained by the lid member locked to the periphery of the opening. In this case, with the lock section thrust in a rotating direction, the lid member can be firmly held by the periphery of the opening of the luminal cavity (by the living body lumen), so that the opening can be occluded. Thus, the internal pressure of the luminal cavity can be effectively restrained from rising and/or maintained constant and/or reduced.

A plurality of the lock sections can be arranged along the outer circumference of the lid member, and each of the lock sections is provided with a thrust-in section oriented along the rotating direction of the lid member.

With the plurality of lock sections thus arranged along the outer circumference of the lid member, the lock sections can be thrust into a plurality of portions of the periphery of the opening of the luminal cavity. Consequently, the lid member can be more reliably locked.

In the above described luminal cavity closing device, the shaft is provided at its distal portion with a torque transmitting section having a roughly conical shape increasing in diameter along the distal direction, and the torque transmitting section supports the outer circumference of the lid member and transmits the torque from the shaft to the lid member.

Where the torque transmitting section supports the outer circumference of the lid member and transmits the torque from the shaft to the lid member, the torque can be transmitted directly to the outer circumference of the lid member which is in contact with the periphery of the opening of the luminal cavity. Therefore, the lid member can be rotated with a small torque, thereby locking the lid member. Accordingly, application of an unnecessary stress to the component parts of the luminal cavity closing device or to the luminal cavity can be obviated.

Further, in the above described luminal cavity closing device, the torque transmitting section includes an annular frame which supports the outer circumference of the lid member, and a plurality of linear frames which interconnect the shaft and the annular frame, and the linear frames are each connected to the lid member, supported by the annular frame, at a position near the lock section.

Where the linear frames are each thus connected to the lid member at a position near the lock section, the torque from the shaft can be more directly transmitted to the lock section thrust into the periphery of the opening of the luminal cavity.

Furthermore, in the above described luminal cavity closing device, the lid member has a hole capable of communicating with the luminal cavity, and the shaft has a support member which is inserted through the hole into the luminal cavity and supports the opening of the luminal cavity.

When the support member is inserted through the hole of the lid member into the luminal cavity, at the time of positioning the lid member at the opening of the luminal cavity, the opening of the luminal cavity can be supported with the support member, by preliminarily inserting the support member into the luminal cavity. Consequently, the lid member can be easily positioned at the opening of the luminal cavity.

In addition, according to another embodiment of the presently disclosed subject matter, an exemplary luminal cavity closing method can include: delivering a shaft to an opening of a luminal cavity formed in a living body lumen via the living body lumen and positioning a lid member attached to a distal portion of the shaft at the opening of the luminal cavity; after the delivery step, transmitting a torque from the shaft to the lid member so as to rotate the lid member and thrusting a lock section into a periphery of the opening of the luminal cavity so as to lock the lid member; and after the locking step, detaching the shaft from the lid member with the lid member being locked to the opening of the luminal cavity, by a detachment mechanism that detachably interconnects the shaft and the lid member.

According to this luminal cavity closing method, an opening of a luminal cavity can be occluded by a simple operation in which the lid member is rotated by the shaft to thrust the lock section into the periphery of the opening of the luminal cavity in the locking step, and the lid member is detached from the shaft by the detachment mechanism in the detachment step. This ensures that flow of blood into the luminal cavity can be restrained by the lid member. In addition, with the lock section thrust into the periphery of the opening of the luminal cavity, the lid member can be firmly held onto the periphery of the opening (onto the living body lumen) of the luminal cavity. As a result, the opening of the luminal cavity can be occluded. Therefore, the internal pressure of the luminal cavity can be effectively restrained from rising.

Thus, an opening of a luminal cavity formed in a living body lumen can be occluded and the internal pressure of the luminal cavity can be effectively restrained or prevented from rising, and possibly even decreased, through a simple operation.

BRIEF DESCRIPTION OF THE DRAWINGS

FIG. 7A is an illustration of a detachment mechanism according to a fifth modification, FIG. 7B is an illustration of a detachment mechanism according to a sixth modification, and FIG. 7C is an illustration of a detachment mechanism according to a seventh modification.

DETAILED DESCRIPTION OF EXEMPLARY EMBODIMENTS

Figure 1:
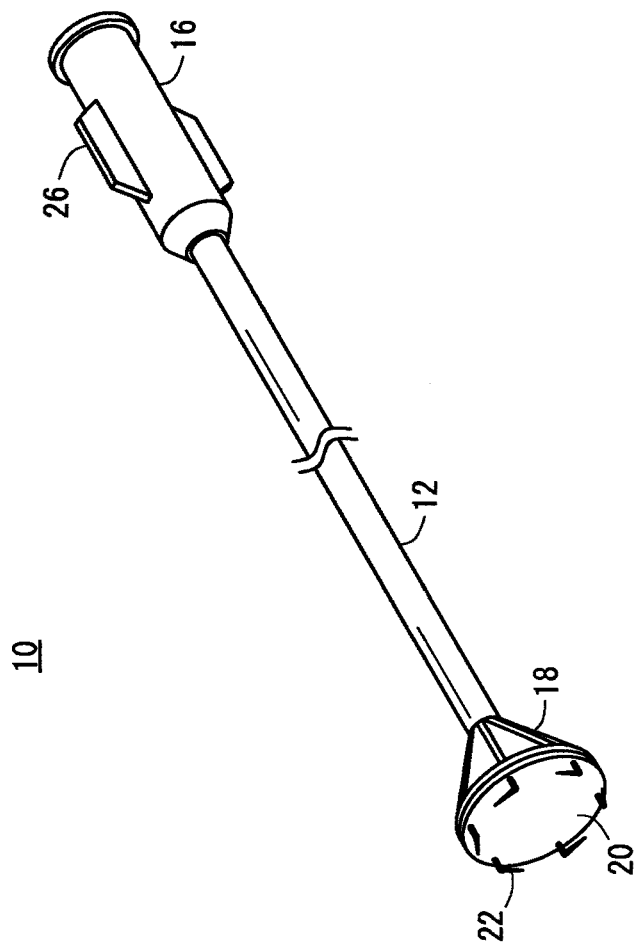
FIG. 1 is a schematic perspective view of a luminal cavity closing device according to an exemplary embodiment of the presently disclosed subject matter.

Now, a luminal cavity closing device made in accordance with principles of the presently disclosed subject matter will be described in detail below in relation to a luminal cavity closing method, by showing an exemplary embodiment and referring to the accompanying drawings.

A luminal cavity closing device 10 is a therapeutic device by which a luminal cavity (aneurysm or varicose or the like) 102 (see FIG. 3A) generated in a blood vessel 100 (living body lumen) is treated through an intravascular interventional technique (a technique for delivering a device to a therapeutic target site through the inside of the blood vessel 100). Particularly, the luminal cavity closing device 10 according to this embodiment can be used to apply a suitable treatment to the luminal cavity 102 (aneurysm) formed in an artery (blood vessel 100) so as to have a comparatively large opening 104.

FIG. 1 is a schematic perspective view showing the general configuration of the luminal cavity closing device 10 according to this embodiment. As shown in FIG. 1, the luminal cavity closing device 10 can include a shaft 12 extending in the axial direction, an operating section 16 provided at the proximal end of the shaft 12, a torque transmitting section 18 provided at the distal end of the shaft 12, and a lid member 20 detachably attached to the torque transmitting section 18. In addition, attachment structures such as hooks 22 capable of being locked to the blood vessel 100 are provided at a distal end surface of the lid member 20.

An operator (a user of the luminal cavity closing device 10) delivers the luminal cavity closing device 10 to a predetermined position by use of a catheter 14 (see FIG. 3A), positions the lid member 20 at the distal end of the shaft 12 at a target part (such as a luminal cavity 102) to be treated in the blood vessel 100, and rotates the lid member 20 in contact with the luminal cavity 102. This makes the hooks 22 of the lid member 20 lock to the periphery of the opening 104 (namely, to a wall part of the blood vessel), whereby the luminal cavity 102 is occluded with this lid member 20.

The shaft 12 of the luminal cavity closing device 10 is formed in a long linear shape (wire-like shape) extending in the axial direction. The shaft 12 may be either hollow or solid in structure, and can have such flexibility so as to be able to easily follow up and along the curvature of the catheter 14 inserted into a tortuous blood vessel 100. The shaft 12 can also have a degree of rigidity so as to enable easy locking of the lid member 20 to the opening 104 of the luminal cavity 102.

In this case, examples of the material constituting the shaft 12 include metals and resins. Examples of the metals include pseudo-elastic alloys (inclusive of superelastic alloys) such as Ni—Ti alloys, shape memory alloys, stainless steels (e.g., all types of SUS such as SUS304, SUS303, SUS316, SUS316L, SUS316J1, SUS316J1L, SUS405, SUS430, SUS434, SUS444, SUS429, SUS430F, SUS302, etc.), cobalt alloys, noble metals such as gold, platinum, etc., tungsten alloys, and carbon-containing materials (inclusive of piano wires). Examples of the resins include polymer materials such as polyolefins (e.g., polyethylene, polypropylene, polybutene, ethylene-propylene copolymers, ethylene-vinyl acetate copolymers, ionomers, or mixtures of two or more of them), polyvinyl chloride, polyamides, polyamide elastomers, polyesters, polyester elastomers, polyurethane, polyurethane elastomers, polyimides, fluororesins, and mixtures of them, which may be used either singly or in combination of two or more of them. The shaft 12 may be composed of a multi-layer tube or the like of a composite material formed from these metals and/or resins. A radiopaque marker may be provided in the vicinity of the distal end of the shaft 12, for enabling recognition of the distal portion under radioscopy.

The size of the shaft 12 is appropriately selected according to the target part to be treated. For example, in the case where the luminal cavity closing device 10 is used for therapy of cerebral aneurysm, the overall length of the shaft 12 is about 800 to 1,500 mm, and the outside diameter is about 0.6 to 3 mm. In addition, depending on the target part to be treated, the overall length of the shaft 12 is about 300 to 2,000 mm, the outside diameter is about 5 to 10 mm, and the inside diameter is about 4 to 9.8 mm.

The operating section 16 connected to a proximal portion of the shaft 12 is formed to be greater in diameter than the shaft 12, so as to be easily gripped by the operator. The operating section 16 is provided at its outer circumferential surface with a pair of wings 26 for enhancing operability for the operator. By gripping the operating section 16, the operator carries out a predetermined operation (advancing and retracting operations and turning operations), thereby moving the distal end side of the shaft 12 guided into the blood vessel 100.

Figure 2A:
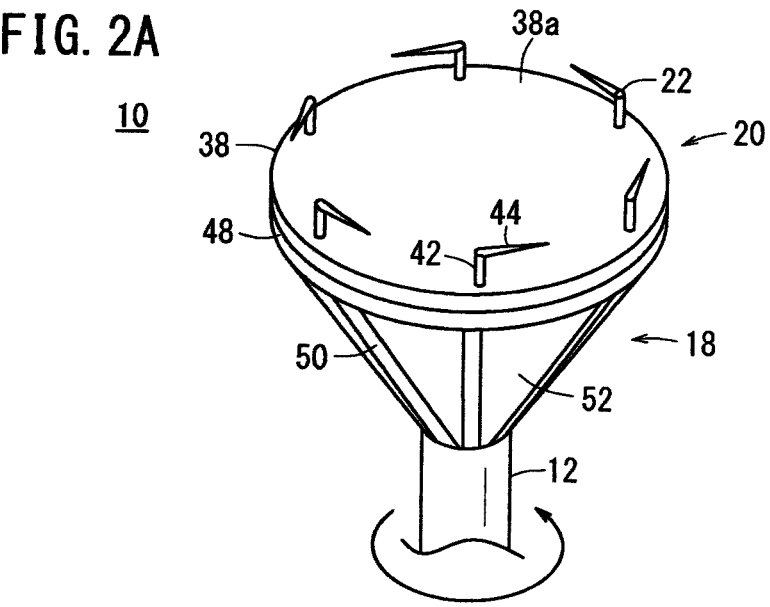
FIG. 2A is a partial enlarged perspective view showing a distal portion of a device body of FIG. 1.
Figure 2B:
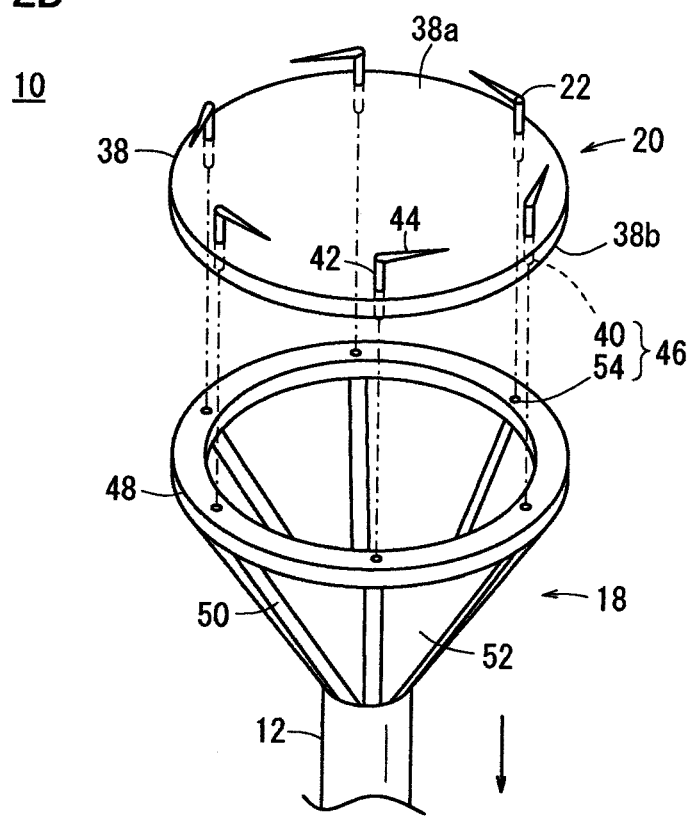
FIG. 2B is a partial enlarged view showing a condition wherein a lid member has been detached from the device body of FIG. 2A.

FIG. 2A is a partial enlarged perspective view showing a distal portion of the luminal cavity closing device 10 of FIG. 1, and FIG. 2B is a partial enlarged view showing a condition wherein the lid member 20 has been detached from the luminal cavity closing device 10 of FIG. 2A. As shown in FIGS. 2A and 2B, the lid member 20 is detachably attached to the distal end (torque transmitting section 18) of the shaft 12. The lid member 20 includes an occlusive section 38 formed as a circular disk-shaped membrane body, the lock section can be formed as a plurality of hooks 22 provided at a distal end surface 38a of the occlusive section 38, and a plurality of proximal end projections 40 can be provided at a proximal end surface 38b of the occlusive section 38.

The occlusive section 38 is designed to have a flat surface area greater than the sectional area of the opening 104 of the luminal cavity 102 which is the target of treatment. This enables the opening 104 to be covered. Incidentally, the size of the opening 104 of the luminal cavity 102 is presumed to vary depending on individual conditions of the disease, etc. Therefore, it may be desirable to prepare a plurality of lid members 20 differing in the flat surface area. The catheter 14 (see FIG. 3A) for delivering the luminal cavity closing device 10 can be formed such that the sectional area of a lumen 28 thereof is greater than the flat surface area of the lid member 20 attached to the shaft 12. This enables the luminal cavity closing device 10 to be easily moved along the axial direction within the lumen 28 while maintaining the flat surface shape of the lid member 20.

The occlusive section 38 can be formed of a material which has a rigidity characteristic so as not to be pushed in by the blood pressure in the state of occluding the opening 104 and which also does not impose an adverse effect on the patient when kept indwelling in the blood vessel 100. In this case, examples of the material used to form the occlusive section 38 include metallic materials such as stainless steels, Ni—Ti alloys, tantalum, nickel, chromium, iridium, tungsten, titanium, and cobalt alloys. In addition, non-biodegradable polymer materials may also be used. Examples of the polymer materials include polyesters such as polyethylene terephthalate, polybutylene terephthalate, etc. and polyester elastomers having these polyesters as building blocks thereof, polyamides such as nylon 6, nylon 12, nylon 66, nylon 610, etc. and polyamide elastomers having these polyamides as building blocks thereof, polyurethanes, polyolefins such as polyethylene, polypropylene, etc. and polyolefin elastomers having these polyolefins as building blocks thereof, polycarbonates such as polyethylene carbonate, polypropylene carbonate, etc., cellulose acetate, cellulose nitrate, and so on. Further, ceramics such as alumina and zirconia may also be employed as the material for the occlusive section 38. Furthermore, mixtures, laminates and the like of the above-mentioned materials can also be used.

The plurality of hooks 22 formed at the distal end surface of the occlusive section 38 function to lock the lid member 20 to the periphery of the opening 104 of the luminal cavity 102. The hooks 22 are disposed near the outer circumference of the flat surface (distal end surface 38a) of the occlusive section 38, at regular intervals along the circumferential direction of the occlusive section 38. The hooks 22 can be formed, for example, of a metallic material such as stainless steel which would not easily be corroded by blood.

The hooks 22 each include a base part 42 projecting shortly in the distal direction from the occlusive section 38, and a sharp part 44 (thrust-in part) bent from the base part 42 at an angle of about 90 degrees and extending by a predetermined length. The amount of projection of the base part 42 of the hook 22 can be smaller than the thickness of a wall part 106 of the blood vessel 100 in which the lid member 20 is to be left indwelling.

On the other hand, the sharp part 44 can be formed in a needle-like shape having a point portion smaller in diameter than the base part 42. The sharp part 44 can be oriented along the circumferential direction of the occlusive section 38 (specifically, in the rotating direction of the lid member 20), in front view (see FIG. 5B) of the lid member 20. Therefore, when the lid member 20 which is in contact with the periphery of the opening 104 of the luminal cavity 102 is rotated about the center of the occlusive section 38, the sharp parts 44 of the hooks 22 can be thrust into the periphery of the opening 104 of the luminal cavity 102. Thus, the lid member 20 is locked to the wall part 106 of the blood vessel 100. Incidentally, though not shown specifically, the hook 22 (sharp part 44) may be formed with a barb so that the hook 22 thrust in the periphery of the opening 104 is prevented from slipping off or backing out.

In addition, the proximal end projections 40 of the lid member 20 are projectingly formed on the side of the proximal end surface 38b of the occlusive section 38 at positions corresponding to the positions where the hooks 22 are arranged. In other words, the proximal end projection 40 can be configured as an integral member extending in the proximal direction from the hook 22. The proximal end projections 40 are disposed near the outer circumference of the proximal end surface 38b, at regular intervals along the circumferential direction of the occlusive section 38. The proximal end projections 40 constitute part of a detachment mechanism 46 by which the lid member 20 is detachably attached to the torque transmitting section 18.

The torque transmitting section 18, to a distal end surface of which the lid member 20 is attached, transmits a torque of the shaft 12 to the lid member 20. The torque transmitting section 18 according to this embodiment is formed in a roughly conical shape, of which a proximal portion is connected to the distal end of the shaft 12, and which gradually increases in diameter along the distal direction from the proximal portion thereof. Specifically, the torque transmitting section 18 includes an annular frame 48 which supports the outer circumference of the lid member 20, a plurality of linear frames 50 which interconnect the shaft 12 and the annular frame 48, and a cover part 52 which is supported by the annular frame 50 and covers the lateral circumferential surface of the conical shape.

The annular frame 48 is a ring-shaped frame body to which the lid member 20 is directly attached, and its outside diameter is approximately equal to the outside diameter of the lid member 20 (occlusive section 38). The annular frame 48 is supported by the plurality of linear frames 50 and the cover part 52, whereby the center of its annular portion is located on the axial line of the shaft 12.

In addition, the distal end surface of the annular frame 48 is formed with a plurality of mounting holes 54, which are arranged along the annular direction (circumferential direction). The mounting holes 54, which constitute a part of the detachment mechanism 46, are formed at regular intervals so as to face the proximal end projections 40 of the lid member 20, and are bored so as to be parallel to the axial direction of the shaft 12. Attendant on mounting of the lid member 20, the proximal end projections 40 are inserted into the mounting holes 54, whereby the proximal end projections 40 are held in firm contact under a comparatively weak frictional force.

The detachment mechanism 46 of the luminal cavity closing device 10 includes the proximal end projections 40 of the lid member 20 and the mounting holes 54 in the torque transmission section 18. With the proximal end projections 40 inserted into the mounting holes 54 along the axial direction of the shaft 12, the lid member 20 is detachably connected to the torque transmitting section 18 (the shaft 12). When a torque is transmitted from the shaft 12 to the torque transmitting section 18 in the condition wherein the lid member 20 is mounted, the torque transmitting section 18 is rotated about its axis, whereby the lid member 20 can be rotated in an accompanying manner. Thus, the hooks 22 of the lid member 20 can be thrust into the periphery of the opening 104 of the luminal cavity 102. Then, when the shaft 12 is retracted (pulled out) in the proximal direction with the lid member 20 being hooked to the opening 104, the proximal end projections 40 are disengaged from the mounting holes 54, whereby the lid member 20 is detached from the torque transmitting section 18 (the shaft 12).

The linear frames 50 of the torque transmitting section 18 can be rectilinear frame elements constituting the lateral circumferential portion of the conical shape, and are configured to transmit the torque of the shaft 12 to the annular frame 48. The plurality of linear frames 50 support the annular frame 48, while being inclined at the same angle from the shaft 12, so that the torque can be evenly transmitted.

In addition, the linear frames 50 are connected to the annular frame 48 at positions proximate to the mounting holes 54 formed in the annular frame 48. Therefore, when the proximal end projections 40 of the lid member 20 are inserted in the mounting holes 54, the linear frames 50 can support annular frame portions near the positions where the hooks 22 are arranged. This ensures that the torque of the shaft 12 is smoothly transmitted through the linear frames 50 to the hooks 22 which are thrust into the periphery of the opening 104.

On the other hand, the cover part 52 of the torque transmitting section 18 constitutes the lateral circumferential portion of the conical shape, and is formed to cover the plurality of linear frames 50. This cover part 52 interconnects the adjacent ones of the linear frames 50 with a comparatively high rigidity, whereby the torque of the shaft 12 is dispersedly transmitted in the circumferential direction to the annular frame 48.

Incidentally, the torque transmitting section 18 is not restricted to the above-mentioned configuration, and various modes can be adopted. For instance, a circular disk-shaped member (not shown) having a flat shape like the lid member 20 may be adopted as the torque transmitting section 18. In this case, the shaft 12 is connected to a central portion of the circular disk-shaped member, whereby the torque of the shaft 12 can be transmitted to the lid member 20 through the circular disk-shaped member. In addition, the torque transmitting section 18 may have a configuration in which, without providing any linear frame 50, a cover part 52 having a comparatively high rigidity is formed (molded) in a conical shape so as to support the annular frame 48.

Figure 3A:
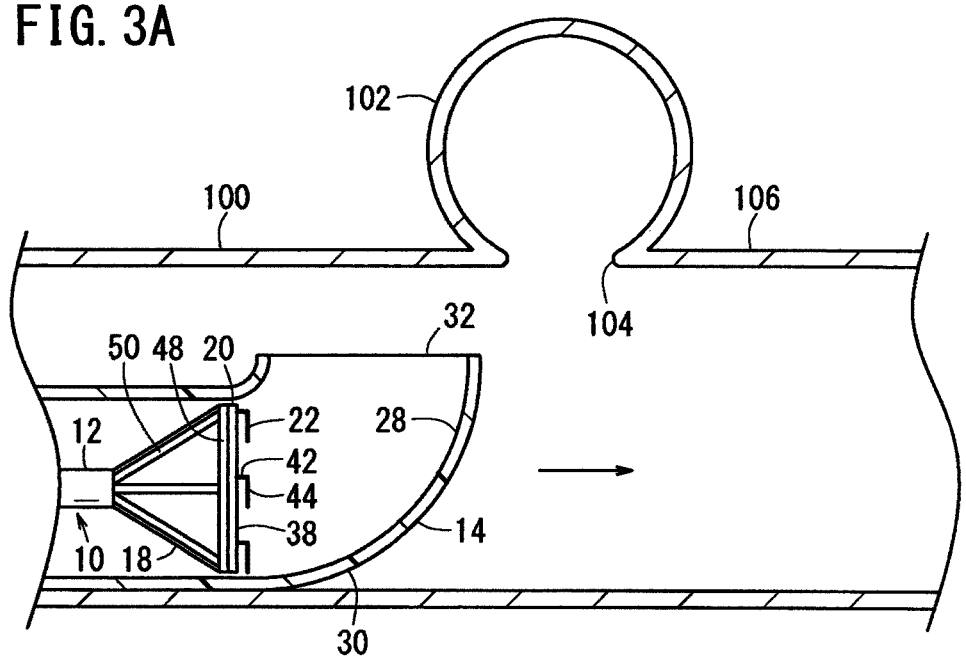
FIG. 3A is a first view illustrating a method of using the luminal cavity closing device of FIG. 1.
Figure 3B:
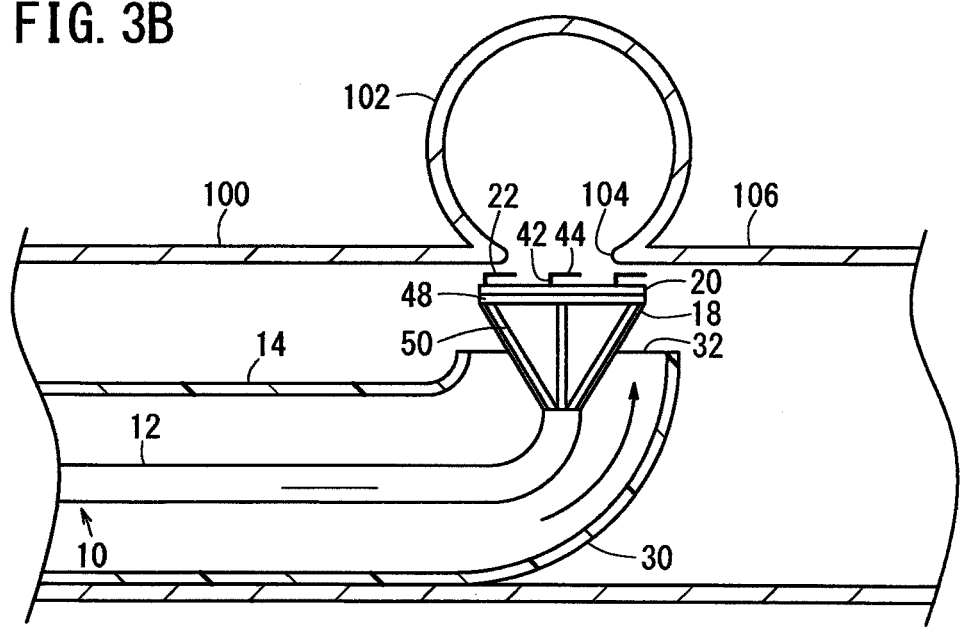
FIG. 3B is a second view illustrating a method of using the luminal cavity closing device of FIG. 1.
Figure 4A:
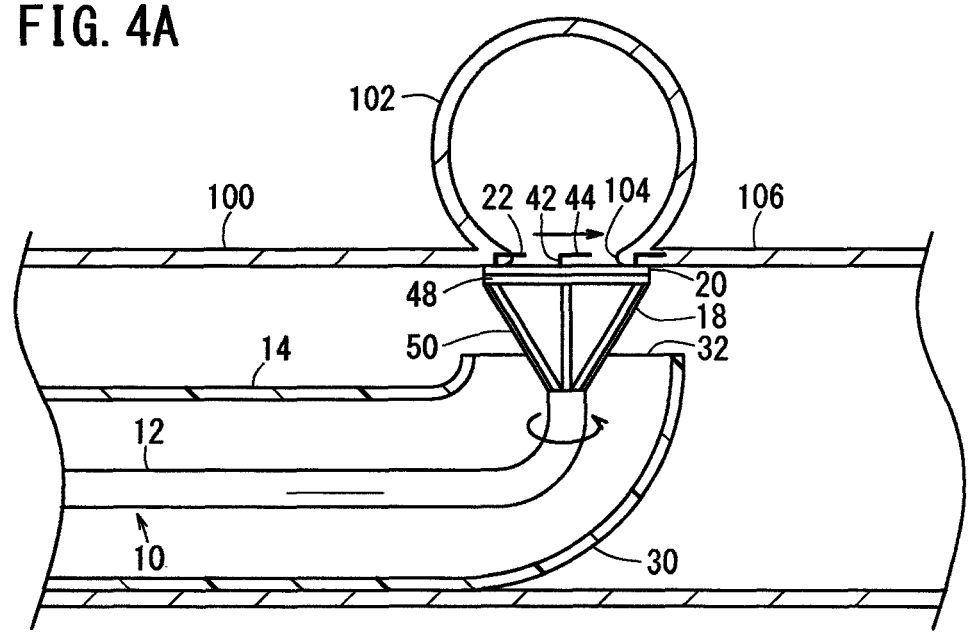
FIG. 4A is a third view illustrating a method of using the luminal cavity closing device of FIG. 1.
Figure 4B:
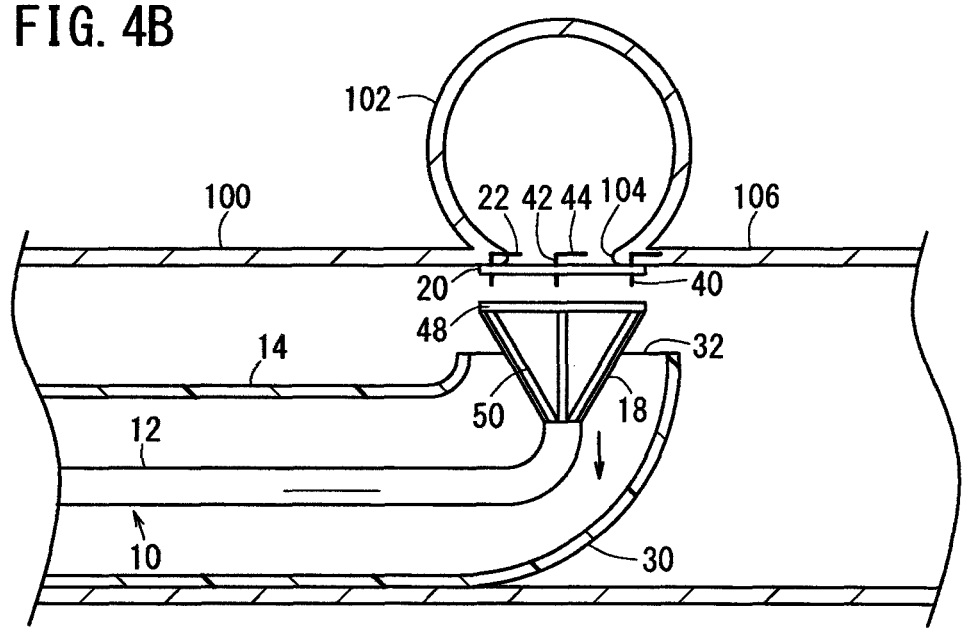
FIG. 4B is a fourth view illustrating a method of using the luminal cavity closing device of FIG. 1.
Figure 5A:
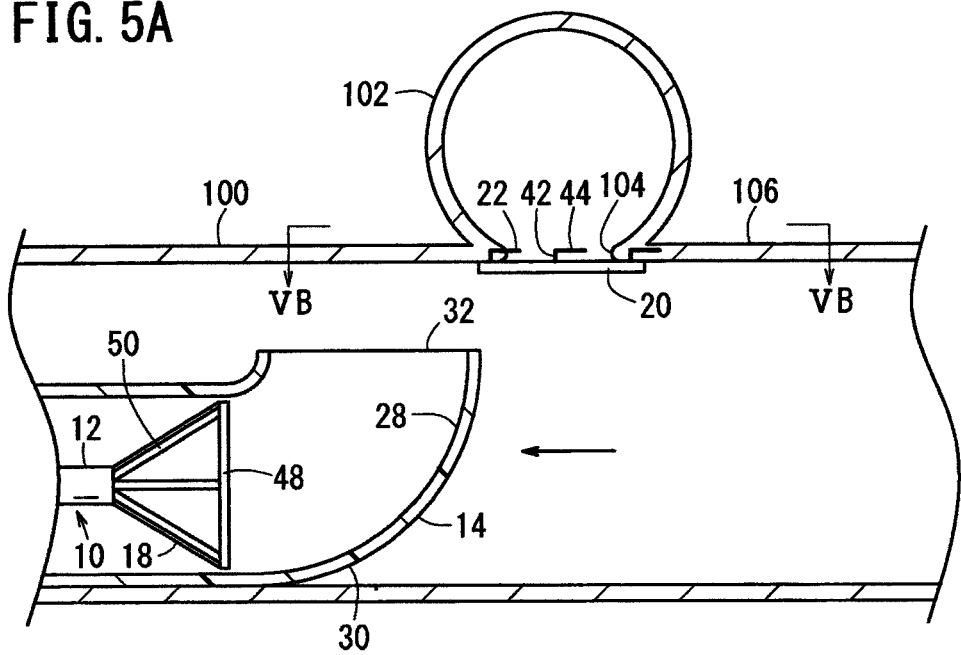
FIG. 5A is a fifth view illustrating a method of using the luminal cavity closing device of FIG. 1.
Figure 5B:
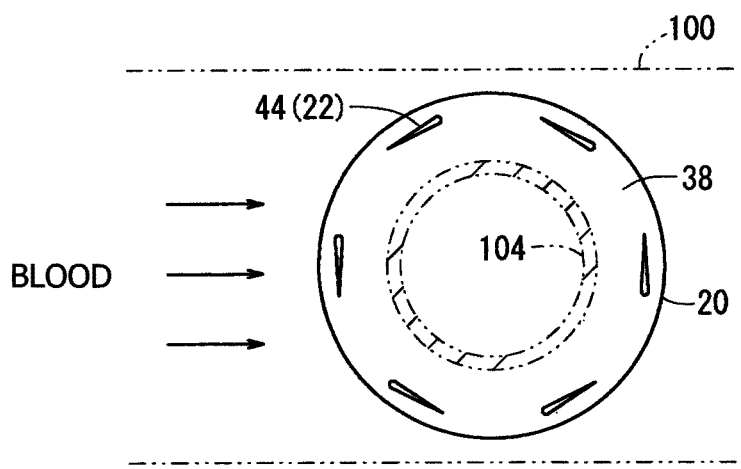
FIG. 5B is a schematic sectional view taken along line VB-VB of FIG. 5A.

The luminal cavity closing device 10 according to this embodiment is fundamentally configured as described above, and its operation and effect will be described below. FIG. 3A is a first view illustrating a method of using the luminal cavity closing device 10, FIG. 3B is a second view illustrating a method of using the luminal cavity device 10, FIG. 4A is a third view illustrating a method of using the luminal cavity device 10, FIG. 4B is a fourth view illustrating a method of using the luminal cavity closing device 10, FIG. 5A is a fifth view illustrating a method of using the luminal cavity closing device 10, and FIG. 5B is a schematic sectional view taken along line VB-VB of FIG. 5A.

As described above, the luminal cavity closing device 10 according to this embodiment is suitably used for therapy of the luminal cavity 102 having a comparatively large opening 104. The luminal cavity 102 is formed, for example, by a process wherein the wall part 106 (e.g., blood vessel wall) of a blood vessel (e.g., artery) is weakened due to arteriosclerosis or the like, and the weakened part is gradually dilated by being pressed by force of the bloodstream. Normally, the luminal cavity 102 is formed in a sac-like shape of the dilated wall part 106, and blood flows into the sac via the opening 104 which communicates with the blood vessel 100. Examples of blood vessels where the luminal cavity 102 may be generated include arteries, veins, and peripheral vessels. Examples of the luminal cavity 102 include cerebral aneurysm, abdominal artery aneurysm, thoracic artery aneurysm, coronary artery aneurysm, popliteal artery aneurysm, femoral artery aneurysm, carotid artery aneurysm, varix, and others.

An example of a luminal cavity closing method using the luminal cavity closing device 10 will now be described in brief. In the exemplary luminal cavity closing method, the following steps are sequentially carried out: a first step (delivery step) in which the luminal cavity closing device 10 is delivered through the blood vessel 100, and its distal end (the lid member 20) is positioned at the opening 104 of the luminal cavity 102; a second step (locking step) in which a torque is transmitted from the shaft 12 to the lid member 20 to rotate the lid member 20, whereby the hooks 22 are thrust into the periphery of the opening 104 of the luminal cavity 102 so as to lock the lid member 20; a third step (detachment step) in which the lid member 20, locked to the opening 104 of the luminal cavity 102, is detached from the shaft 12; and a fourth step (retraction step) in which the luminal cavity closing device 10 is retracted (withdrawn) from the inside of the blood vessel 100. Thus, the lid member 20 is left indwelling in the blood vessel 100, in the state of occluding the opening 104. Now, these steps will be described in detail below.

Delivery Step

In the delivery step, first, a guiding catheter (not shown) is percutaneously inserted into the blood vessel 100 from a predetermined position (for example, a femoral part or the like), and is advanced to a position proximate to the site of generation of the luminal cavity 102 along a guide wire (not shown), which has previously been inserted into the blood vessel 100. Then, the guide wire is pulled out, after which the position of the guiding catheter is fixed, and the catheter 14 configured as a microcatheter is inserted into the lumen of the guiding catheter, to deliver the catheter 14 to the site of generation of the luminal cavity 102.

The catheter 14 has a distal portion which is, for example, preliminarily provided with a gently curved shape (for example, Judkins right shape) or provided with a shape-basis tendency to curve at an angle of about 90 degrees. In this case, when the distal portion of the catheter 14 is pushed out of the opening of the guiding catheter, the catheter 14 is so deformed that it is curved at a curved portion 30 by substantially (almost or exactly) 90 degrees from its proximal-side straight portion and that its distal opening 32 comes to front on the wall part 106 of the blood vessel 100, as shown in FIG. 3A. Incidentally, the catheter 14 may be so configured as to have its distal portion curved by a wire, for example.

In addition, the catheter 14 shown in FIGS. 3A to 5A has a shape suitable for treatment of a luminal cavity 102 formed at a lateral circumferential surface of a blood vessel 100 extending rectilinearly. This, however, is not restrictive. For the luminal cavity closing device 10, a catheter with a suitable shape is selected according to the part to be treated (the part where the luminal cavity 102 is generated). For instance, in the case where the luminal cavity 102 is formed at a part where the blood vessel 100 is bifurcated in a Y-shaped form, it suffices to use a straight catheter without any curved portion 30 and to face the distal opening 32 of the catheter to the opening 104 of the luminal cavity 102.

The catheter 14 is further guided through the blood vessel 100, based on the operator's operation, to dispose the distal opening 32 at a position in register (e.g., adjacent to or in contact with) with the opening 104 of the luminal cavity 102. At the time of delivery of the catheter 14, the luminal cavity closing device 10 can be preliminarily inserted in the lumen 28 of the catheter 14. Particularly, the lid member 20 and the torque transmitting section 18 provided at the distal end of the shaft 12 may preliminarily be set in a stand-by state near the curved portion 30 of the catheter 14, which enables the delivery step to be carried out at an enhanced efficiency.

After the distal opening 32 of the catheter 14 is positioned to face the opening 104 of the luminal cavity 102, as shown in FIG. 3B, the catheter 14 is fixed. In this condition, the shaft 12 of the luminal cavity closing device 10 in the stand-by state is moved forward (distally) relative to the catheter 14. In this forward movement, the shaft 12 is moved forward while curving along the curved portion 30 of the catheter 14, and its distal end (the lid member 20 and the torque transmitting section 18) is fed out via the distal opening 32 of the catheter 14.

With the shaft 12 advanced further, the lid member 20 which is then exposed through the distal opening 32 of the catheter 14 comes into contact with the wall part 106 of the blood vessel 100 in such a manner as to cover the opening 104 of the luminal cavity 102. In this case, since the hooks 22 of the lid member 20 are bent at 90 degrees, it is ensured that in spite of the contact of the lid member 20 with the wall part 106, puncture of the wall part 106 by the hooks 22 is obviated or prevented. Therefore, if the flat surface portion of the lid member 20 (the occlusive section 38) is not in register with the opening 104 of the luminal cavity 102, repositioning can be carried out by once retracting the shaft 12 and then moving the catheter 14 again. This enables the lid member 20 to be assuredly positioned so as to cover the opening 104 of the luminal cavity 102 and be put into contact with the wall part 106 in this condition.

Locking Step

After the delivery step, a locking step is carried out as shown in FIG. 4A. In the locking step, the operator rotates the operating section 16 of the luminal cavity closing device 10, thereby rotating the shaft 12 connected to the operating section 16. The torque of the shaft 12 is transmitted to the torque transmitting section 18 provided at the distal end of the shaft 12, whereby the torque transmitting section 18 is rotated about the axis of the shaft 12. Therefore, the torque is transmitted also to the lid member 20 mounted to the torque transmitting section 18, so that the lid member 20 as a whole is rotated about a central portion of the occlusive section 38. By this rotation, the hooks 22 provided near the outer circumference of the lid member 20 are thrust into the periphery of the opening 104 (into the wall part 106 of the blood vessel 100).

Here, the amount of rotation of the lid member 20 is approximately equal to the amount of thrust-in of the sharp parts 44 of the hooks 22. Since the sharp parts 44 extend only a short distance, a little rotation of the operating section 16 enables the sharp parts 44 as a whole to be thrust into the wall part 106. In addition, since the linear frames 50 of the torque transmitting section 18 are connected to the portions at which the hooks 22 are arranged, the torque of the shaft 12 can be smoothly transmitted to the hooks 22. Furthermore, since the surface of the occlusive section 38 fronts on the opening 104 attendantly on the positioning of the lid member 20 in the delivery step, an outer circumferential portion of the occlusive section 38 makes surface contact with the periphery of the opening 104. Accordingly, the plurality of hooks 22 can be simultaneously thrust into the wall part 106, attendant on the rotation of the lid member 20.

When the sharp parts 44 as a whole are thrust into the wall part 106, the base parts 42 and the wall part 106 make contact with each other, whereby the rotation is stopped. A load torque upon the stoppage of the rotation is transmitted to the operator on a sensory basis. Consequently, the lid member 20 is locked to the periphery of the opening 104 so as to cover the opening 104.

Detachment Step

After the locking step, a detachment step is carried out as shown in FIG. 4B. In the detachment step, the operating section 16 (namely, the luminal cavity closing device 10) is retracted, with the lid member 20 being locked to the periphery of the opening 104. In this instance, since the hooks 22 are caught on the wall part 106 of the blood vessel 100, the lid member 20 does not follow the retraction of the luminal cavity closing device 10 but remains locked to the periphery of the opening 104. Therefore, the proximal end projections 40 are easily disengaged from the mounting holes 54, and the lid member 20 is detached from the torque transmitting section 18. In this way, with the detachment mechanism 46 according to this embodiment, the lid member 20 can be easily detached by pulling out the torque transmitting section 18 in the axial direction relative to the lid member 20. In addition, the shaft 12 from which the lid member 20 has been detached is contained as it is in the lumen 28 of the catheter 14.

Retraction Step

After the detachment step, a retraction step is carried out as shown in FIG. 5A. In the retraction step, the operating section 16 is retracted, whereby the luminal cavity closing device 10 is withdrawn into and contained in the catheter 14. Thereafter, the luminal cavity closing device 10 and the catheter 14 are retracted as one body, and pulled out of the blood vessel 100. Thus, only the lid member 20 can be left at the opening 104 of the luminal cavity 102, thereby occluding the luminal cavity 102 (e.g., tightly closing the opening 104 without leaving any gap) with the lid member 20.

Here, as shown in FIG. 5B, in the lid member 20 left indwelling in the periphery of the opening 104, the sharp parts 44 thrust into the wall part 106 are oriented in the circumferential direction (rotating direction) of the lid member 20. Specifically, the hooks 22 of the lid member 20 are locked by being rotated in a predetermined rotating direction (in FIG. 5B, counterclockwise direction), so that the locked state can be maintained unless a torque in the reverse direction (clockwise direction) is exerted. Therefore, even when the lid member 20 receives a load from the blood flowing in the axial direction through the blood vessel 100, the lid member 20 is prevented from slipping off (peeling off), and the opening 104 can be occluded firmly with the lid member 20.

As above-described, the luminal cavity closing method using the luminal cavity closing device 10 according to this embodiment makes it possible to occlude the opening 104 of the luminal cavity 102 easily and assuredly. With the luminal cavity 102 thus occluded, the blood can be prevented from flowing into the luminal cavity 102, and the blood present inside the luminal cavity 102 may coagulate with the lapse of time, so that rupture of the luminal cavity 102 and the like can be prevented from occurring.

Incidentally, the lid member 20 left indwelling at the opening 104 of the luminal cavity 102 and the detachment mechanism 46 for the detachment of the lid member 20 are not restricted to the above-mentioned configurations; naturally, other modes can also be adopted. Now, modifications of the above-mentioned configurations will be described below.

Figure 6B:
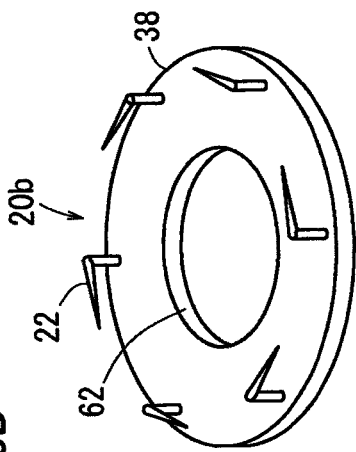
FIG. 6B is an illustration of a lid member according to a second modification.
Figure 6D:
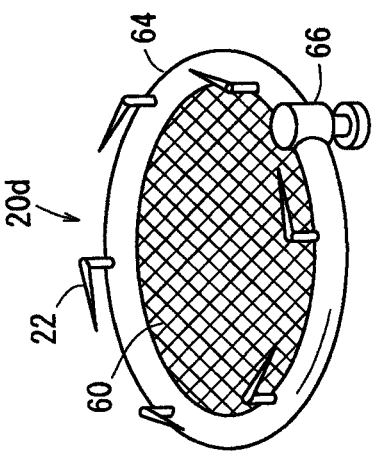
FIG. 6D is an illustration of a lid member according to a fourth modification.
Figure 6A:
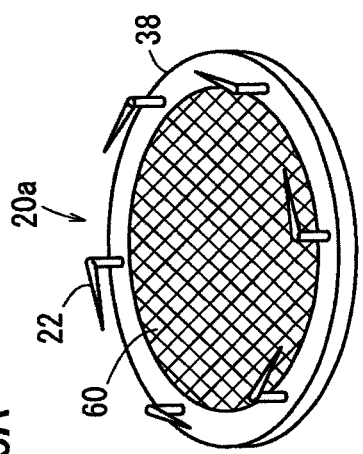
FIG. 6A is an illustration of a lid member according to a first modification.
Figure 6C:
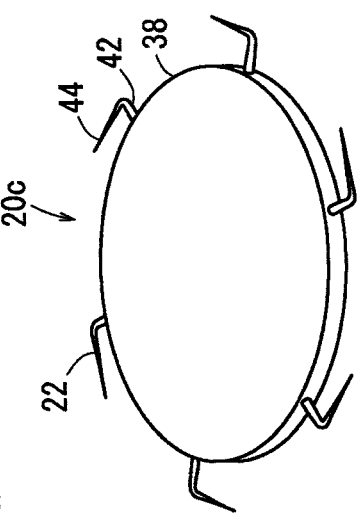
FIG. 6C is an illustration of a lid member according to a third modification.

FIG. 6A is an illustration of a lid member 20a according to a first modification, FIG. 6B is an illustration of a lid member 20b according to a second modification, FIG. 6C is an illustration of a lid member 20c according to a third modification, and FIG. 6D is an illustration of a lid member 20d according to a fourth modification.

As shown in FIG. 6A, the lid member 20a according to the first modification has a structure in which a flat surface portion of the occlusive section 38 for occluding the opening 104 of the luminal cavity 102 is formed in a meshed form (mesh part 60). This mesh part 60 permits blood to flow therethrough. When the opening 104 is thus occluded with the mesh part 60, also, the flow of blood into the luminal cavity 102 can be suppressed sufficiently, and rupture of the luminal cavity 102 and the like can be prevented from occurring.

As shown in FIG. 6B, the lid member 20b according to the second modification has a through-hole 62 in a flat surface part of the occlusive section 38 for occluding the opening 104 of the luminal cavity 102. Even though the lid member 20b is thus provided with the through-hole 62, its aperture area is smaller than that of the opening 104 of the luminal cavity 102, so that the flow of blood into the luminal cavity 102 can be suppressed. Incidentally, while an example wherein one through-hole 62 is formed is shown in FIG. 6B, a plurality of such through-holes 62 may be formed.

The annular member of the lid member 20b may be formed from an expandable and contractible material. At the time of attaching the lid member 20b to the luminal cavity closing device 10, the lid member 20b is in the state of being expanded in the circumferential direction as compared with a natural state. When the lid member 20b is locked to the periphery of the opening 104 by the hooks 22 and a torque is applied thereto, the lid member 20b is detached from the annular frame 48 which previously supported the outer circumference of the lid member 20b, and is left indwelling at the opening 104. In this instance, the expandable and contractible lid member 20b is circumferentially contracted, so that the through-hole 62 is contracted in diameter. With the through-hole 62 thus contracted in diameter, the quantity of blood flowing into the luminal cavity 102 via the opening 104 can be suppressed. In addition, where the luminal cavity closing device 10 has a support member or members 82 which will be described later, the size (e.g., diameter) of the support member(s) 82 can be reduced.

As shown in FIG. 6C, the lid member 20c according to the third modification has a structure wherein the base parts 42 of the hooks 22 are extended horizontally from a lateral circumferential surface of the occlusive section 38, and the sharp parts 44 are oriented in the rotating direction of the lid member 20 with respect to the base parts 42. Even though the hooks 22 are thus extended horizontally, the hooks 22 can be thrust into the wall part 106 of the blood vessel 100, since the blood vessel 100 is tubular in shape. In short, the hooks 22 disposed on the lid member 20 desirably have a structure wherein the sharp parts 44 to be thrust into the wall part 106 are oriented in the rotating direction of the lid member 20, and the inclination angle (extending direction) of the base parts 42 and the like factors may be set as required.

As shown in FIG. 6D, the lid member 20d according to the fourth modification has a structure in which a ring-shaped outside frame element 64 is provided with an adjustment part 66 capable of adjusting the circumference of the lid member 20. The outside frame element 64 is so structured that the inside diameter of its one end to be connected to the adjustment part 66 is greater than the outside diameter of its other end, and the outside frame element 64 at the other end can be gradually inserted into the outside frame element 64 on the adjustment part 66 side. The adjustment part 66 is used to modify the circumference of the outside frame element 64, by screwing a predetermined position of the outside frame element 64. By the modification of the circumference, the flat surface area of the lid member 20 can be set according to the sectional area of the opening 104 of the luminal cavity 102. This ensures that the flat surface area of the lid member 20 can be appropriately adjusted according to various luminal cavities 102 differing in the size with respect to opening 104. Consequently, the opening 104 can be assuredly occluded.

FIG. 7A is an illustration of a detachment mechanism 46a according to a fifth modification, FIG. 7B is an illustration of a detachment mechanism 46b according to a sixth modification, and FIG. 7C is an illustration of a detachment mechanism 46c according to a seventh modification.

As shown in FIG. 7A, the detachment mechanism 46a according to the fifth modification has a screw engagement structure of a male screw part 70 and a female screw part 72. Specifically, the occlusive section 38 is formed with the male screw part 70 at the proximal end surface 38b thereof, and the annular frame 48 is formed with the female screw part 72, whereby the lid member 20 is put into screw engagement with the annular frame 48. The lid member 20 can be detached by a method in which after the torque transmitting section 18 is rotated in the direction of thrust-in of the hooks 22 to lock the lid member 20 to the periphery of the opening 104 of the luminal cavity 102, the torque transmitting section 18 is rotated further in the same direction to release the screw engagement between the male screw part 70 and the female screw part 72. Incidentally, this detachment mechanism 46 may have a structure in which the annular frame 48 is provided with the male screw part 70, and the lid member 20 is provided with the female screw part 72.

In addition, the detachment mechanism 46b according to a sixth modification has a structure in which hook-shaped parts 74 formed on the proximal end surface of the lid member 20 and engagement parts 76 formed on the annular frame 48 are engaged with each other. For instance, as shown in FIG. 7B, the hook-shaped part 74 is formed in an L-shaped form extending from the proximal end surface of the lid member 20, and an extension end part 74a thereof is oriented in the rotating direction (the same direction as that in which the sharp parts 44 of the hooks 22 are oriented). On the other hand, the engagement part 76 is projected in the distal direction from the torque transmitting section 18, and is provided with an insertion hole 78 bored in the direction coinciding with the rotating direction. In this detachment mechanism 46, as the lid member 20 is mounted, the insertion holes 78 hold the hook-shaped parts 74 with a predetermined holding force.

When the torque is transmitted from the shaft 12 in this holding state (the mounted state of the lid member 20), the holding force causes the lid member 20 to be rotated in an accompanying manner, whereby the hooks 22 can be thrust into the periphery of the opening 104 of the luminal cavity 102. In the condition wherein the lid member 20 has been locked to the periphery of the opening 104 and the rotation is stopped, the torque transmitting section 18 is rotated further in the same direction, and the engagement between the insertion holes 78 and the hook-shaped parts 74 can thus be released (disengaged), and the lid member 20 detached from the torque transmitting section 18. Thus, according to the detachment mechanism 46b having the hook-shaped parts 74 and the engagement parts 76, also, it is possible to lock the lid member 20 to the periphery of the opening 104 of the luminal cavity 102 and to detach the lid member 20 while in the locked state.

As shown in FIG. 7C, in the detachment mechanism 46c according to the seventh configuration, extension end parts 74b of the hook-shaped parts 74 formed at the proximal end surface of the occlusive section 38 may be oriented in the direction reverse to the direction of the sharp parts 44. In this case, the engagement parts 76 and the hook-shaped parts 74 can be engaged with each other with a weak engaging force. Specifically, when the torque transmitting section 18 is rotated in the direction of the sharp parts 44, the engagement parts 76 are caught on the hook-shaped parts 74, and the torque of the torque transmitting section 18 can be smoothly transmitted to the lid member 20. On the other hand, after the lid member 20 is locked to the periphery of the opening 104 of the luminal cavity 102, it is possible, by rotating the torque transmitting section 18 in the direction reverse to the direction in which the sharp parts 44 are oriented, to release the engagement between the hook-shaped parts 74 and the engagement parts 76 and to detach the lid member 20 from the torque transmitting section 18.

Figure 8A:
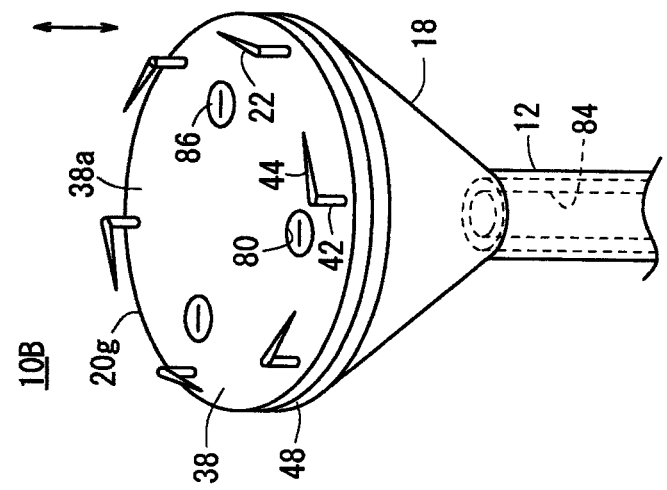
FIG. 8A is an illustration of a distal portion of a device body according to an eighth modification.
Figure 8B:
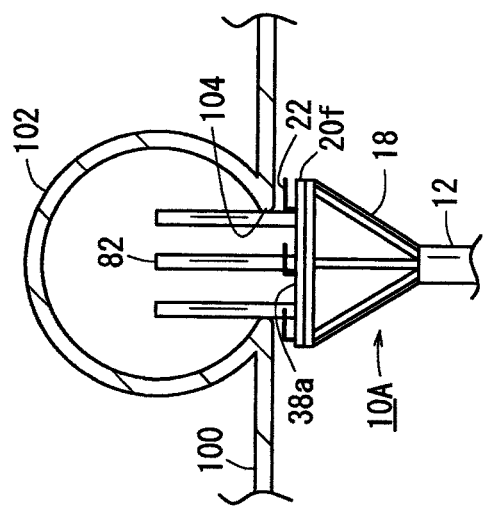
FIG. 8B is an illustration of a condition wherein the device body of FIG. 8A is positioned at a luminal cavity.
Figure 8C:
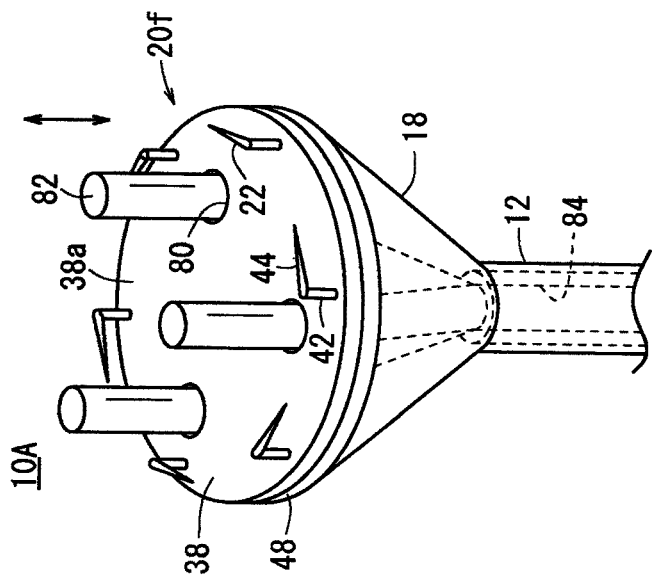
FIG. 8C is an illustration of a distal portion of a device body according to a ninth modification.

FIG. 8A is an illustration of a distal portion of a luminal cavity closing device 10A according to an eighth modification, FIG. 8B is an illustration of a condition wherein the luminal cavity closing device 10A of FIG. 8A is positioned at the luminal cavity 102, and FIG. 8C is an illustration of a distal portion of a luminal cavity closing device 10B according to a ninth modification.

As shown in FIG. 8A, the luminal cavity closing device 10A according to the eighth modification has a structure in which a lid member 20f is provided with plural (in FIG. 8A, three) holes 80 and provided with a plurality of support members 82 capable of projecting through the holes 80. The holes 80 are disposed on the inner periphery (e.g., radial when member 20 is circular) direction side as compared to the hooks 22 provided in the out periphery (e.g. outer circumferential) direction, and guide the projection of the support members 82. In addition, the luminal cavity closing device 10A (shaft 12) is formed therein with a hollow part 84 (lumen) extending in the axial direction, and the support members 82 are slidably disposed in the hollow part 84. The support members 82 have their proximal portions extending proximally through the hollow part 84 to come out via the proximal end of the operating section 16 of the shaft 12. With the proximal portions operated by the operator, the support members 82 are advanced and retracted. When advanced, the support members 82 project through the holes 80.

Thus, the luminal cavity closing device 10A is provided with the holes 80 and the support members 82, whereby the lid member 20f can be easily positioned in the periphery of the opening 104 of the luminal cavity 102. Specifically, in positioning the lid member 20f in the periphery of the opening 104, as shown in FIG. 8B, the support members 82 are projected from the lid member 20f with a predetermined timing, to be inserted through the opening 104 into the luminal cavity 102. This ensures that the lid member 20f can be positioned with the support members 82 supporting the opening 104. In addition, when the shaft 12 is rotated, the hooks 22 can be thrust into the periphery of the opening 104 in the condition wherein the opening 104 is supported by the support member 82. As a result, the lid member 20 can be easily locked.

As shown in FIG. 8C, the luminal cavity closing device 10B according to the ninth modification, has a structure wherein check valves 86 are provided at a plurality of holes 80 of a lid member 20g, and the shaft 12 is formed therein with the hollow part 84 (lumen) extending in the axial direction. A suction device (not shown) is provided at the proximal end of the hollow part 84, whereby blood flowing or existing into the luminal cavity 102 can be sucked through the holes 80 and the hollow part 84. Thus, the luminal cavity closing device 10B ensures that the opening 104 can be occluded by the lid member 20g in the condition wherein the luminal cavity 102 has been contracted by the suction of the blood. In addition, the lid member 20g left indwelling at the opening 104 of the luminal cavity 102 ensures that the check valves 86 can prevent blood from flowing again into the luminal cavity 102.

As described above, the luminal cavity closing device 10 and the luminal cavity closing method according to this embodiment makes it possible to occlude the opening 104 of the luminal cavity 102 by a simple process wherein the lid member 20 is rotated by the shaft 12 to thrust the hooks 22 into the periphery of the opening 104 of the luminal cavity 102, after which the lid member 20 is detached from the shaft 12 by the detachment mechanism 46. In this case, with the hooks 22 thrust into the wall part 106 of the blood vessel 100, the lid member 20 can be firmly held on the periphery of the opening 104 of the luminal cavity 102 (the wall part 106 of the blood vessel 100), so that the opening 104 of the luminal cavity 102 can be occluded. Accordingly, a rise in the internal pressure of the luminal cavity 102 can be effectively restrained, prevented and possibly reversed.

In addition, with the plurality of hooks 22 arranged along the outer circumference of the lid member 20, the hooks 22 can be thrust into a plurality of portions of the periphery of the opening 104 of the luminal cavity 102, whereby the lid member 20 can be more assuredly locked.

Furthermore, since the torque transmitting section 18 supports the outer circumference of the lid member 20 and transmits the torque from the shaft 12 to the lid member 20, the torque can be transmitted directly to the outer circumference of the lid member 20 which is in contact with the periphery of the opening 104 of the luminal cavity 102. Therefore, it is possible to rotate the lid member 20 with a small torque and thereby lock the lid member 20. Accordingly, application of an unnecessary stress to the component parts of the luminal cavity closing device 10 or to the luminal cavity 102 can be obviated.

While the presently disclosed subject matter has been described with reference to exemplary embodiments above, the disclosed subject matter is not restricted to these embodiments, and various alterations are possible within the scope of the invention.

For instance, the outside diameter of the lid member 20 may be greater than the inside diameter of the lumen 28 of the catheter 14. In this case, a configuration may be adopted wherein the torque transmitting section 18 is flexible, and the lid member 20 is inserted into the catheter 14 in the manner of being folded so that the lid member 20 will be automatically expanded (unfolded) upon being fed out through the distal opening 32 of the catheter 14. The attachment structure is shown as being in the form of hooks 22. However, other known attachment structures and methods could be used, such as clamps, adhesives, cauterization, etc. Similarly, other known detachment mechanism structures and methods can be utilized, such as magnets, meltable attachment structures, soluble attachment structures, frangible structures, etc. It should also be noted that any of the above mentioned modifications can be used in conjunction with each other in various combinations and either simultaneously or separately.

What is claimed is:

1. A luminal cavity closing device comprising:
    a flexible shaft extending in an axial direction;
    a lid member attached to a distal end of the shaft, the lid member being rotatable according to a torque transmitted from the shaft, and the lid member including a lock section configured as hooks each having a base part and a sharp part,
    wherein the hooks are configured to thrust, attendantly on rotation in a first direction, into a periphery of an opening of a luminal cavity formed in a living body lumen, to thereby lock the lid member to the periphery of the opening of the luminal cavity, and
    wherein the sharp part of each hook is arranged along an outer circumference of the lid member at substantially regular intervals and is oriented in a circumferential direction and in a rotating direction of the lid member, the sharp part of each hook also being pointed in a direction parallel with a tangent to a periphery of the lid member; and
    a detachment mechanism by which the lid member is detachably attached to the shaft, and through which the torque is transmitted to the lid member during operation of the device, such that the shaft is detachable from the lid member when the lid member is locked to the periphery of the opening of the luminal cavity.

2. The luminal cavity closing device according to claim 1, wherein the lock section includes a plurality of lock structures arranged along an outer circumference of a distal surface of the lid member, and each of the lock structures is provided with a thrust-in section oriented in a rotating direction of the lid member.

3. The luminal cavity closing device according to claim 1, wherein a distal portion of the shaft includes a torque transmitting section having a roughly conical shape increasing in diameter along a distal direction; and
    the torque transmitting section is configured to support an outer circumference of the lid member and to transmit the torque from the shaft to the lid member.

4. The luminal cavity closing device according to claim 3, wherein the torque transmitting section includes an annular frame configured to support the outer circumference of the lid member, and a plurality of linear frames which interconnect the shaft and the annular frame; and
    the linear frames are each connected to the annular frame at a position such that a longitudinal axis of each of the linear frames intersects a respective lock structure of the lock section.

5. The luminal cavity closing device according to claim 1, wherein the lid member has a hole configured to communicate with the luminal cavity, and
    the shaft has a support member which extends through the hole into the luminal cavity during operation and is configured to support the opening of the luminal cavity.

6. The luminal cavity closing device according to claim 1, wherein the detachment mechanism includes a plurality of posts extending integrally from the lock section and substantially perpendicular to a bottom surface of the lid member, and apertures located in an annular frame connected to the shaft.

7. The luminal cavity closing device according to claim 1, wherein the lid member includes a mesh material.

8. The luminal cavity closing device according to claim 1, wherein the lid member includes at least one aperture extending completely through the lid member in a direction substantially perpendicular to a distal-most surface of the lid member.

9. The luminal cavity closing device according to claim 1, wherein the lid member includes an adjustment mechanism configured to change an outermost peripheral length of the lid member.

10. The luminal cavity closing device according to claim 1, wherein the lock section includes a plurality of lock structures that each extend radially away from a center of the lid member and are located about an outermost peripheral circumferential surface.

11. The luminal cavity closing device according to claim 1, wherein the detachment mechanism includes one of male and female screw threads located on the lid member, and one of female and male screw threads located on an annular rim connected to the shaft.

12. The luminal cavity closing device according to claim 1, wherein the detachment mechanism is configured such that continuous rotation of the shaft in the first direction causes the shaft to disconnect from the lid member.

13. The luminal cavity closing device according to claim 1, wherein the detachment mechanism is configured such that rotation of the shaft in a direction opposite to the first direction causes the shaft to disconnect from the lid member.

14. A luminal cavity closing device comprising:
a flexible shaft having a longitudinal axis and including a torque transmitting section located at a distal portion of the shaft;
a lid member attached to the torque transmitting section, the lid member having a distal surface facing away from the shaft and including a substantially planar surface substantially perpendicular to the longitudinal axis of the shaft, the lid member including a lock section configured as hooks each having a base part and a sharp part and configured to attach to a periphery of an opening of a luminal cavity formed in a living body lumen, to thereby lock the lid member to the periphery of the opening of the luminal cavity,
wherein the sharp part of each hook is arranged along an outer circumference of the lid member at substantially regular intervals and is oriented in a circumferential direction and in a rotating direction of the lid member, and the sharp part of each hook is pointed in a direction parallel with a tangent to a circumference of the distal surface of the lid member; and
a detachment mechanism by which the lid member is detachably attached to the shaft, and through which torque is transmitted to the lid member during operation of the device, such that the shaft is detachable from the lid member when the lid member is locked to the periphery of the opening of the luminal cavity.

15. The luminal cavity closing device according to claim 14,
wherein the torque transmitting section has a substantially conical shape increasing in diameter along the longitudinal axis of the shaft; and
the torque transmitting section is attached to an outer circumference of the lid member and configured to transmit the torque from the shaft to the lid member.

16. The luminal cavity closing device according to claim 14, wherein the distal surface of the lid member is substantially circular.

17. A luminal cavity closing method comprising:
delivering a shaft to an opening of a luminal cavity formed in a living body lumen via the living body lumen and positioning a lid member attached to a distal portion of the shaft at the opening of the luminal cavity and including a lock section configured as hooks each having a base part and a sharp part,
wherein the sharp part of each hook is arranged along an outer circumference of the lid member at substantially regular intervals and is oriented in a circumferential direction and in a rotating direction of the lid member;
after delivering and positioning, transmitting a torque from the shaft to the lid member so as to rotate the lid member and thrusting the sharp part of the hooks into a periphery of the opening of the luminal cavity thereby locking the lid member to the periphery of the opening of the luminal cavity; and
after locking, detaching the shaft from the lid member while the lid member is locked to the periphery of the opening of the luminal cavity, by using a detachment mechanism that detachably interconnects the shaft and the lid member.

18. The luminal cavity closing method of claim 17, wherein detaching the shaft from the lid member includes sliding a post located in one of the lid member and shaft out of engagement with an aperture located in an opposite one of the shaft and lid member.

19. The luminal cavity closing method of claim 17, wherein locking the lid member to the periphery of the opening of the luminal cavity includes thrusting the hooks into engagement with the periphery of the opening of the luminal cavity, wherein the hooks are pointed in a direction parallel with a tangent to an outer periphery of the lid member and are located on the lid member.

* * * * *